(12) United States Patent
Urano (10) Patent No.: US 9,933,378 B2
(45) Date of Patent: Apr. 3, 2018

(54) COIL UNIT AND APPARATUS FOR DETECTING FOREIGN MATTER

(71) Applicant: TDK CORPORATION, Tokyo (JP)

(72) Inventor: Takashi Urano, Tokyo (JP)

(73) Assignee: TDK CORPORATION, Tokyo (JP)

( * ) Notice: Subject to any disclaimer, the term of this patent is extended or adjusted under 35 U.S.C. 154(b) by 558 days.

(21) Appl. No.: 14/554,811

(22) Filed: Nov. 26, 2014

(65) Prior Publication Data

US 2015/0145529 A1    May 28, 2015

(30) Foreign Application Priority Data

Nov. 28, 2013   (JP) ................................ 2013-246451
Oct. 3, 2014    (JP) ................................ 2014-204702

(51) Int. Cl.
*G01N 27/02*    (2006.01)
*H02J 5/00*     (2016.01)
(Continued)

(52) U.S. Cl.
CPC .......... *G01N 27/025* (2013.01); *B60L 11/182* (2013.01); *H01F 38/14* (2013.01);
(Continued)

(58) Field of Classification Search
CPC ........ G01N 27/025; H02J 5/005; H02J 7/025; H02J 50/60; H02J 50/12; H02J 50/40;
(Continued)

(56) References Cited

U.S. PATENT DOCUMENTS 9,465,064 B2    10/2016  Roy et al.
2009/0278552 A1  11/2009  Jakkula et al.
(Continued)

FOREIGN PATENT DOCUMENTS

JP    2012-16125 A    1/2012
JP    2013-099090 A   5/2013
(Continued)

OTHER PUBLICATIONS

May 4, 2015 Search Report issued in European Patent Application No. 14195201.0.
(Continued)

*Primary Examiner* — Minh Phan
*Assistant Examiner* — Brent J Andrews
(74) *Attorney, Agent, or Firm* — Oliff PLC (57) ABSTRACT

A power feeding coil unit (a coil unit) is provided with a power feeding coil (a coil for power transmission) and an apparatus for detecting foreign matter. The apparatus for detecting foreign matter is provided with a plurality of resonators having a resonator coil and capacitor and also an excitation coil for exciting the plurality of resonators. The plurality of resonators are disposed in rows and columns to cover at least an area interlinking with a magnetic flux generated by the power feeding coil. The excitation coil makes resonators adjacent in a row direction and a column direction among the plurality of resonators to generate an alternating magnetic field with resonance frequencies different from each other within a frequency band in which the power feeding coil is not excited.

2 Claims, 9 Drawing Sheets

(51) Int. Cl.
*H02J 50/60* (2016.01)
*H02J 50/12* (2016.01)
*H01F 38/14* (2006.01)
*H02J 7/02* (2016.01)
*B60L 11/18* (2006.01)

(52) U.S. Cl.
CPC .............. *H02J 5/005* (2013.01); *H02J 7/025* (2013.01); *H02J 50/12* (2016.02); *H02J 50/60* (2016.02); *B60L 2270/147* (2013.01); *Y02T 10/7005* (2013.01); *Y02T 10/7072* (2013.01); *Y02T 90/122* (2013.01); *Y02T 90/14* (2013.01)

(58) Field of Classification Search
CPC ........ H01F 38/14; B60L 11/182; B60L 11/18; G01V 3/104
See application file for complete search history.

(56) References Cited

U.S. PATENT DOCUMENTS

| | | | |
|---|---|---|---|
| 2012/0326523 A1* | 12/2012 | Fukushima | H02J 5/005 307/104 |
| 2013/0094598 A1 | 4/2013 | Bastami | |
| 2013/0099592 A1 | 4/2013 | Abe | |
| 2013/0241302 A1 | 9/2013 | Miyamoto et al. | |
| 2013/0257168 A1 | 10/2013 | Singh | |
| 2014/0015329 A1* | 1/2014 | Widmer | G01D 5/2006 307/104 |
| 2014/0084857 A1 | 3/2014 | Liu et al. | |

FOREIGN PATENT DOCUMENTS

| | | |
|---|---|---|
| JP | 2013-192390 A | 9/2013 |
| WO | 2014/011788 A1 | 1/2014 |
| WO | 2014/095722 A2 | 6/2014 |

OTHER PUBLICATIONS

May 6, 2015 Search Report issued in European Application No. 14195246.5.

U.S. Appl. No. 14/554,967, filed Nov. 26, 2014 in the name of URANO.

Nov. 21, 2016 Office Action Issued in U.S. Appl. No. 14/554,967.

May 3, 2017 Office Action Issued in U.S. Appl. No. 14/554,967.

\* cited by examiner

COIL UNIT AND APPARATUS FOR DETECTING FOREIGN MATTER

The present invention relates to a coil unit and an apparatus for detecting foreign matter.

BACKGROUND

The contactless power transmission in which the power is supplied without using a power cord is attracting attentions. The conventional contactless power transmission is mainly the type based on the electromagnetic induction. It is expected that this technique can be applied to various fields.

In view of the circumstance shown above, such a project is being studied that an electric vehicle is provided with a power receiving coil at its bottom part (power receiving side) and a high power (for example, several kilowatt to several tens of kilowatt) is transmitted in a contactless manner from a power feeding coil on the ground (power feeding side). If the contactless power transmission can be utilized, then the power can be transmitted without mechanically coupling power feeding side to power receiving side.

However, if some foreign matter are present in the gap between the power feeding coil and the power receiving coil when the power is being transmitted in a contactless manner, concerns rise that when the foreign matter is a metal, an eddy current will generate due to the magnetic flux passing through the foreign metal, and when the foreign matter is a magnetic body, there will be a hysteresis loss due to the magnetic flux passing through the foreign magnetic body, so that the foreign matter may be heated.

As a way to avoid the heating problem, Patent Document 1 has suggested a detecting apparatus with a detecting part. Specifically, the detecting part is provided with one or a plurality of magnetic coupling elements which is/are composed of a plurality of coils. It measures the electric parameters related to the magnetic coupling element(s) or a circuit containing at least the magnetic coupling element(s) and then determines whether a foreign matter that may generate heat due to the magnetic flux is present based on the changes of these electric parameters.

PATENT DOCUMENT

Patent Document 1: JP-A-2013-192390

SUMMARY

However, with respect to the technique disclosed in Patent Document 1, a plurality of detecting coils (magnetic coupling elements) are disposed without gaps to eliminate the dead area where the foreign metal cannot be detected, wherein the plurality of detecting coils are connected to the capacitor for resonance and resonates with a given frequency. In this respect, several resonance frequencies are present for each detecting coil (magnetic coupling element) so that the measurement becomes difficult. Further, the Q value of each detecting coil is significantly lowered and the measuring accuracy becomes worse. Thus, a problem is there that the accuracy in detecting the foreign metal is deteriorated.

Therefore, the present invention is provided in view of the related problems. The present invention aims to provide a coil unit with a better accuracy in detecting foreign matter and an apparatus for detecting foreign matter with a better accuracy in detecting foreign matter when the power is transmitted in a contactless manner.

In order to solve the technical problems mentioned above, the coil unit of the present invention is characterized in that it is a coil unit used for contactless power transmission from power feeding side to power receiving side. The coil unit is provided with a coil for power transmission and an apparatus for detecting foreign matter. The apparatus for detecting foreign matter is provided with a plurality of resonators having a resonance coil and a resonance capacitor and also an excitation coil which excites the plurality of resonators. The plurality of resonators are disposed in rows and columns so as to cover at least an area interlinking with a magnetic flux generated by the coil for power transmission. The excitation coil makes resonators adjacent with each other in a row direction and a column direction among a plurality of resonators to generate an alternating magnetic field with resonance frequencies different from each other within a frequency band in which the coil for power transmission is not excited.

In the present invention, the excitation coil makes the resonators adjacent with each other in the row direction and the column direction among the plurality of resonators to generate the alternating magnetic field with resonance frequencies different from each other within a frequency band in which the coil for power transmission is not excited. Thus, even if the plurality of resonators are disposed without gaps in an area for metal detection, each resonator can be prevented from influencing each other. In this respect, each resonator is prevented from generating multiple resonance frequencies so that the decrease of Q value will be inhibited. As a result, the accuracy in detecting metals will be improved when power is transmitted in a contactless manner.

It is preferable that the excitation coil makes one resonator and the resonators which is disposed surrounding it among the plurality of resonators, to generate an alternating magnetic field with resonance frequencies different from each other. In this case, even if the plurality of resonators are disposed without gaps in an area for metal detection, each resonator can be further prevented from influencing each other. So each resonator is practically prevented from generating multiple resonance frequencies, the decrease of Q value will be further inhibited. Therefore, the accuracy in detecting metals will be further improved when power is transmitted in a contactless manner.

Preferably, the apparatus for detecting foreign matter is further provided with a plurality of detecting coils and each of the plurality of detecting coils is disposed so as to be magnetically coupled to each resonator of the plurality of resonators. As such, since the Q values of the plurality of resonators can be indirectly measured without connecting a means for Q value measurement directly to the plurality of resonators, the Q values of the plurality of resonators can be further prevented from decreasing without changing the resonance frequencies of the plurality of resonators.

The apparatus for detecting foreign matter is characterized in that it is an apparatus for detecting foreign matter for a detection of foreign matter and is provided with a plurality of resonators having a resonance coil and a resonance capacitor and also an excitation coil which excites the plurality of resonators. The plurality of resonators are placed in rows and columns in an in-plane direction. The excitation coil makes resonators adjacent with each other in a row direction and a column direction among the plurality of resonators, to generate an alternating magnetic field with resonance frequencies different from each other of a frequency band.

In the present invention, the excitation coil makes the resonators adjacent in the row direction and the column direction to generate the alternating magnetic field among the plurality of resonators with resonance frequencies different from each other of a frequency band. Thus, even if the plurality of resonators are disposed without gaps in an area for metal detection, each resonator can be prevented from influencing each other. In this respect, each resonator is prevented from generating multiple resonance frequencies so that the decrease of Q value will be inhibited. As a result, the accuracy in detecting metals will be improved.

In the present invention, a coil unit with an improved accuracy in detecting foreign matter and an apparatus for detecting foreign matter with an improved accuracy in detecting foreign matter when power is transmitted in a contactless manner can be provided.

DETAILED DESCRIPTION OF EMBODIMENTS

The embodiments for carrying out the present invention will be described in detail with reference to the drawings. However, the present invention is not limited to these embodiments to be described below. Further, the constituent elements described below contain those easily thought of by one skilled in the art and those substantially the same. In addition, the same reference numeral refers to the same element or an element having the same function, and repeated descriptions will be omitted.

Figure 1:
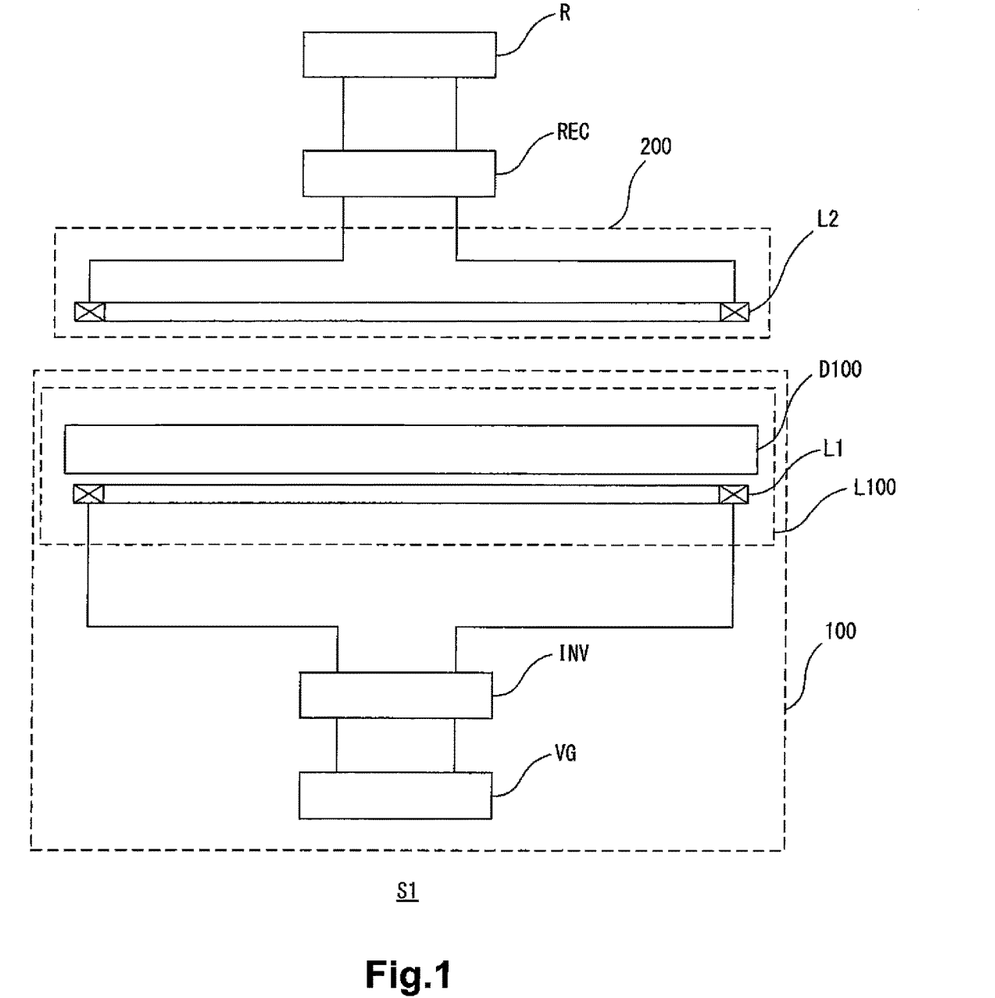
FIG. 1 is a schematic view showing the apparatus, to which the coil unit of the present invention is applied, for contactless power transmission together with a load.

First of all, the overall structure of the apparatus S1 for contactless power transmission to which the coil unit of the preferable embodiments is applicable will be described with reference to FIG. 1 before the coil unit of the preferable embodiments in the present invention. FIG. 1 is a schematic view showing the apparatus, to which the coil unit of the preferable embodiments is applied, for contactless power transmission together with the load. In addition, the coil unit of the present invention can be used as any one of a power feeding coil unit in a power feeding apparatus and a power receiving coil unit in a power receiving apparatus. However, in the following embodiments, the coil unit of the present invention will be described in examples in which the coil unit is applied as the power feeding coil unit in a power feeding apparatus.

As shown in FIG. 1, the apparatus S1 for contactless power transmission is provided with a power feeding apparatus 100 and a power receiving apparatus 200. Here, the apparatus S1 for contactless power transmission is described in an example in which the apparatus S1 is used as a power feeding apparatus for supplying power to a moving object such as an electric vehicle.

The power feeding apparatus 100 is provided with a voltage source VG, a power conversion circuit INV and a power feeding coil unit L100. The voltage source VG feeds a direct current to the power conversion circuit INV to be described later. The voltage source VG is not particularly restricted as long as it outputs a direct current. For example, the power supply can be a direct-current power supply from a rectified and stabilized commercial alternating-current power supply, a secondary battery, a direct-current power supply with power generated via solar energy, or a switching power supply such a switching converter.

The power conversion circuit INV converts the direct current supplied from the voltage source VG to an alternating current and then supplies the alternating voltage to the power feeding coil unit L100 to be described later. In other words, the power conversion circuit INV functions as an inverter. In addition, the power conversion circuit INV can be composed of, for example, a switching circuit with multiple switching elements being bridge connected (not shown in the figures). The switching element forming the switching circuit can be, for example, an element such as MOS-FET (metal oxide semiconductor-field effect transistor), IBGT (insulated gate bipolar transistor) or the like.

The power feeding coil unit L100 functions as a power feeding part for transmitting the alternating current in a contactless manner to the power receiving apparatus 200, which is to be described later. The power feeding coil unit L100 is disposed below the ground or at somewhere near the ground. Further, the specific structure of the power feeding coil unit L100 will be described below.

The power receiving apparatus 200 is provided with a power receiving coil L2 and a rectification circuit REC. As in the present embodiment, when the apparatus S1 for contactless power transmission is applicable to a power feeding apparatus for supplying power to a moving object such as an electric vehicle, the power receiving apparatus 200 is provided on the moving object. Here, the moving object provided with the power receiving apparatus 200 can be an electric vehicle or a hybrid vehicle utilizing the power from a secondary battery.

The power receiving coil L2 functions as a power receiving part for receiving the alternating power supplied from the power feeding coil unit L100 in a contactless manner.

The power receiving coil L12 is disposed at the bottom part of the electric vehicle.

The rectification circuit REC rectifies the alternating current received by the power receiving coil L2 to a direct current and then outputs the direct current to a load R. The rectification circuit REC is composed of, for example, a bridge diode and a capacitor for voltage stabilization (both not shown in the figures). The alternating voltage output from the power receiving coil L2 is subjected to a full-wave rectification by a bridge diode, and then the resultant voltage is stabilized by a capacitor for voltage stabilization. Here, when the apparatus S1 for contactless power transmission is applicable to a power feeding apparatus for supplying power to a moving object such as an electric vehicle, the load R is composed of a charger (not shown) and a battery (not shown) provided in the moving object. The charger functions to control the charging process by charging the battery with a constant current-constant voltage (CCCV) by a direct current rectified by the rectification circuit REC. The battery is not particularly restricted as long as it is capable of saving power. For example, the battery can be a secondary battery (a lithium ion battery, a lithium polymer battery, a Nickel-Metal Hydride battery or the like) or a capacity element (an electrical double-layered capacitor or the like).

With such a structure, the apparatus S1 for contactless power transmission can be provided with which the power is transmitted in a contactless manner from the power feeding coil unit L100 in the power feeding apparatus 100 to the power receiving coil L2 in the power receiving apparatus 200.

The First Embodiment

Figure 2:
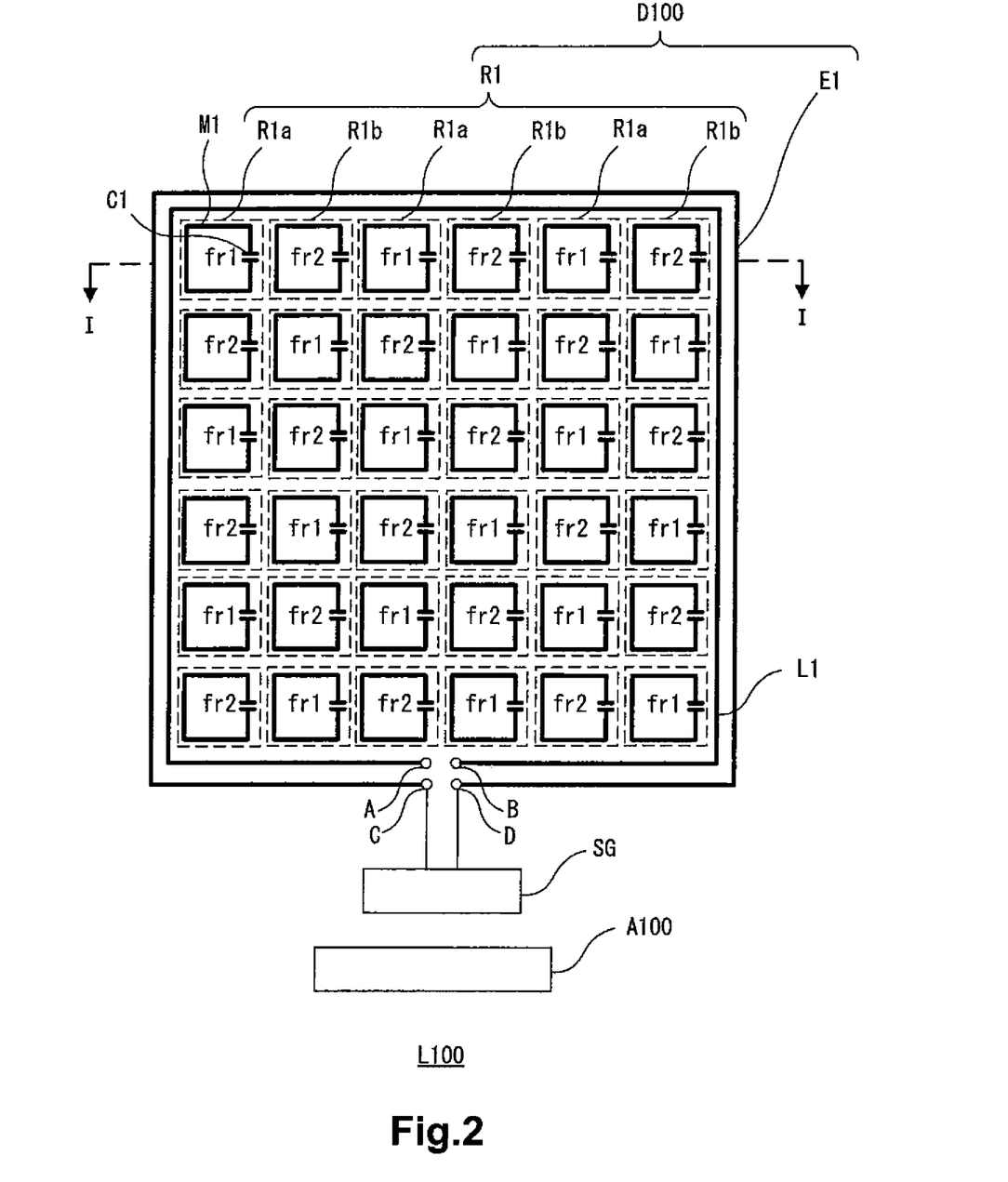
FIG. 2 is a schematic constitutional view showing the power feeding coil unit of the first embodiment viewed from the top in the present invention.
Figure 3:
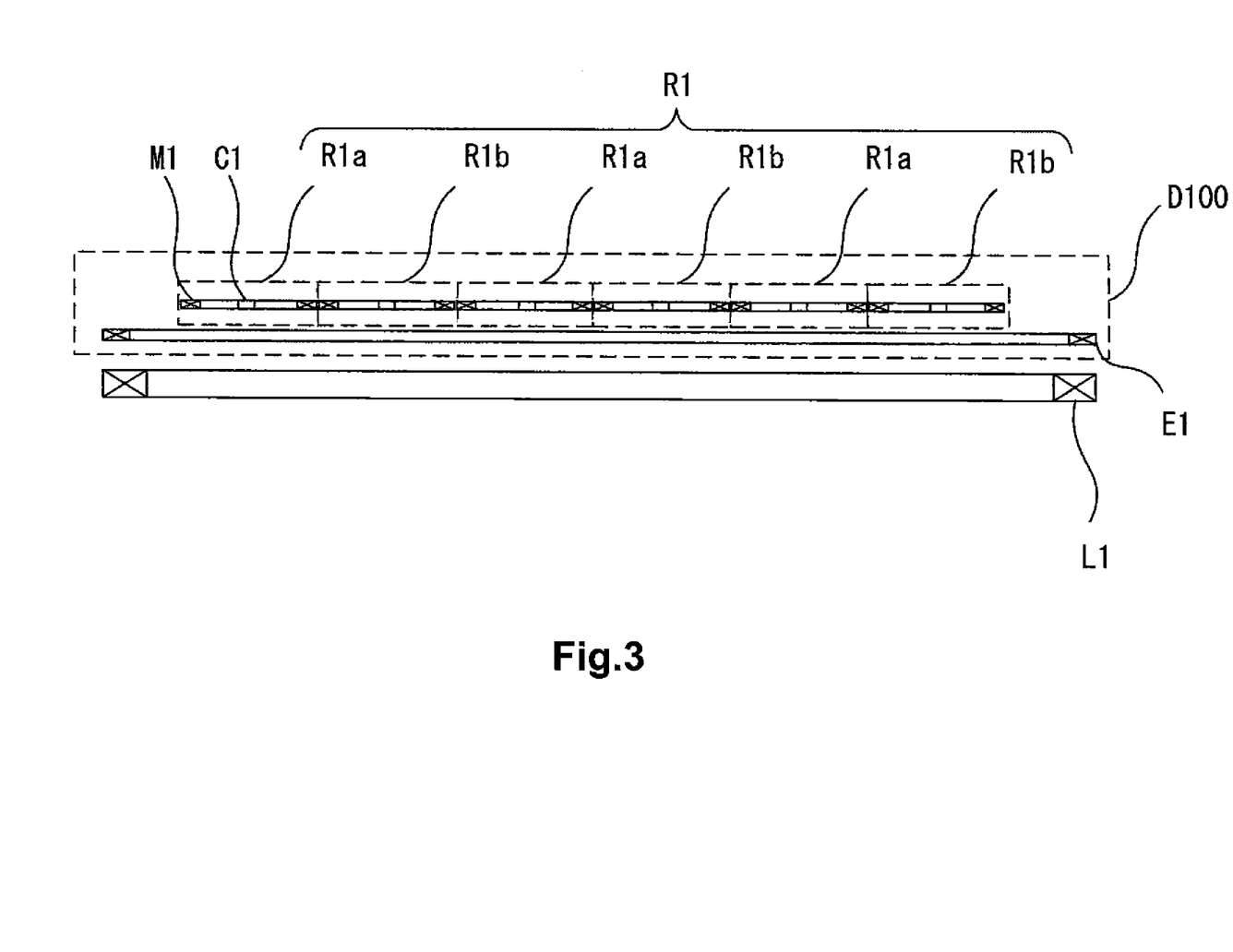
FIG. 3 is a schematic end face view showing the cutting section of the power feeding coil unit along the I-I line in FIG. 2.

Hereinafter, the structure of the power feeding coil unit L100 of the first preferable embodiment of the present invention will be described in detail with reference to FIG. 2 and FIG. 3. FIG. 2 is a schematic constitutional view showing the power feeding coil unit of the first embodiment viewed from the top in the present invention. FIG. 3 is a schematic end face view showing the cutting section of the power feeding coil unit along the I-I line in FIG. 2.

As shown in FIG. 2, the power feeding coil unit L100 is provided with a power feeding coil L1 (the coil for power transmission), an apparatus D100 for detecting foreign matter, a signal generator SG and a frequency response analyzer A100.

As shown in FIG. 2, the power feeding coil L1 is substantially square and is formed by, for example, winding a litz wire into several turns to several dozen of turns, wherein the litz wire is obtained by twisting about 2000 insulated φ0.1 (mm) copper lines. In other words, the power feeding coil L1 is one with an in-plane spiral structure. In the power feeding coil L1, the terminal A at the end where the winding starts and the terminal B at the end where the winding ends are connected to the power conversion circuit INV. With such a structure, when the power feeding coil L1 provides an alternating voltage with a given driving frequency from the power conversion circuit INV, an alternating current will flow and an alternating magnetic field will be generated. Then, an electromotive force is generated in the power receiving coil L2 via the alternating magnetic field. That is to say, the power feeding coil L1 functions as one for transmitting power in a contactless manner to the power receiving coil L2. At that time, the driving frequency of the alternating voltage fed to the power feeding coil L1 is set to be, for example, 20 [kHz] to 200 [kHz].

As shown in FIG. 3, the apparatus D100 for detecting foreign matter is disposed at one side of the power feeding coil L1 which faces the power receiving coil L2. That is, the apparatus D100 for detecting foreign matter is disposed between the power feeding coil L1 (power feeding side) and the power receiving coil L2 (power receiving side). For instance, the apparatus D100 for detecting foreign matter is composed of copper-clad multilayered substrates and is provided with a plurality of resonators R1 and an excitation coils E1.

The plurality of resonators R1 are disposed in rows and columns in order to at least cover the area interlinking with the magnetic flux generated by the power feeding coil L1. In other words, the plurality of resonators R1 are placed in rows and columns in the in-plane direction as shown in FIG. 2. More specifically, the plurality of resonators R1 are disposed to cover the area defined by the wound wires of the power feeding coil L1. In the present embodiment, 36 resonators R1 are placed in 6 rows×6 columns. That is, the area where the plurality of resonators R1 are disposed becomes the area for metal detection. The plurality of resonators R1 are each formed by each resonance coil M1 and each resonance capacitor C1. As shown in FIG. 2, the resonance coil M1 presents to be substantially square and is formed by, for example, pattern printing 4 turns of coils on a layer of the copper-clad multilayered substrate at the side of the power receiving coil L2 in a direction in which the power feeding coil L1 faces the power receiving coil L2. The resonance capacitor C1 and the resonance coil M1 are connected in series to form a resonance circuit. The resonance capacitor C1 can be, for example, a stacked ceramic capacitor, and the electrostatic capacity of the resonance capacitor C1 is set to be several hundreds of picofarad to several thousands of picofarads. Further, if a minute foreign metal is to be detected such as a coin of about φ10 mm, each resonator R1 can be made as a substantial square with a size of 10 mm×10 mm. In addition, the plurality of resonators R1 can also be disposed in rows and columns to cover a wider area than that defined by the wound wire of the power feeding coil L1. In that case, not only the foreign matter on the power feeding coil L1 but also those surrounding the power feeding coil L1 can be detected. Anyway, if the area where the plurality of resonators R1 are disposed in rows and columns can cover at least the area interlinking with the magnetic flux generated by the power feeding coil L1, it can be set at will.

The plurality of resonators R1 with the structure mentioned above are composed of two kinds of resonators, i.e., the resonator R1a and the resonator R1b. Specifically, each of the resonator R1a and the resonator R1b has a single resonance frequency of the frequency band in which the power feeding coil L1 will not be excited, and the two single resonance frequency are respectively set as the resonance frequency fr1 and fr2 which are different from each other. For example, the resonance frequency fr1 of the resonator R1a is set to be 3000 [kHz] and the resonance frequency fr2 of the resonator R1b is set to be 6000 [kHz]. The resonators R1a and the resonators R1b are alternatively disposed to be adjacent in the row direction and the column direction. In other words, the resonators R1a are not adjacent to each other in the row direction and the column direction and the resonators R1b are not adjacent to each other in the row direction and the column direction. Here, if the resonators with the same resonance frequency are next to each other in the row direction and the column direction, the mutual inductance will be changed and several resonance frequencies will generate because resonance coils of the adjacent resonators will be magnetically coupled with each other.

Also, the Q value of the resonance coil in each resonator will significantly decrease. In contrast, in the present embodiment, the resonance frequency fr1 of the resonator R1a and the resonance frequency fr2 of the resonator R1b, which are adjacent to each other in the row direction and the column direction, is set to be different, so no interaction is present near the resonance frequency fr1 of the resonator R1a or near the resonance frequency fr2 of the resonator R1b and the resonator R1a and the resonator R1b respectively have a single resonance frequency. In addition, the Q value of the resonance coil M1 of the resonator R1a and the Q value of the resonance coil M1 of the resonator R1b can be prevented from decreasing. Further, it is preferably that the resonator R1a and the resonator R1b are not disposed to be adjacent in the row direction and the column direction in the whole area for metal detection. However, if the effect of the present invention can be provided, the resonators R1a can be placed to be adjacent in the row direction or the column direction in part of the area for metal detection, so do the resonators R1b.

As shown in FIG. 2, the excitation coil E1 is substantially square and is formed by, for example, pattern printing 3 turns of coils on a layer of the copper-clad multilayered substrate at the side of the power receiving coil L1 in a direction in which the power feeding coil L1 faces the power receiving coil L2. The pattern of the excitation coil E1 is formed outside the area defined by the wound wire of the power feeding coil L1. Also, the end where the pattern of the excitation coil E1 starts (i.e., the terminal C) and the end where the pattern ends (i.e., the terminal D) are connected to the signal generator SG to be described later. With such a structure, the excitation coil E1 is capable of receiving the sine wave signals output from the signal generator SG and is then excited to generate a magnetic field. As such, the resonance coils M1 of the plurality of resonators R1 will be excited by the magnetic field generated by the excitation coil E1.

The signal generator SG provides two sine wave signals of different frequencies alternatively to the excitation coil E1 with a certain interval (such as every 100 ms). The frequency of each of the two sine wave signals is set to be the same with the resonance frequency fr1 of the resonator R1a or the resonance frequency fr2 of the resonator R1b. That is, in the two sine wave signals, one of the sine wave signal was set to have a frequency of 3000 [kHz] which is the same as the resonance frequency fr1 of the resonator R1a, and the other one is set to have a frequency of 6000 [kHz] which is the same as the resonance frequency fr2 of the resonator R1b. As described above, the excitation coil E1 receives the sine wave signal output from the signal generator SG and is then excited to generate a magnetic field. An electromotive force is generated via this magnetic field so that the current flows to the resonance coils M1 of the plurality of resonators R1. At that time, the resonance frequency of the resonator R1a is set to be 3000 [kHz], so the resonator R1a comes into the resonance state and a resonance current flows only when the signal generator SG outputs a sine wave signal of 3000 [kHz]. Further, since the resonance frequency of the resonator R1b is set to be 6000 [kHz], the resonator R1b comes into the resonance state and a resonance current flows only when the signal generator SG outputs a sine wave signal of 6000 [kHz]. In this respect, the frequencies of these two sine wave signals with which the signal generator SG excites the excitation coil E1 are set as a high frequency having an order of magnitude different from that of the driving frequency of the power feeding coil L1. In other words, the frequencies of these two sine wave signals output by the signal generator SG with which the excitation coil E1 is excited are set to be within a frequency band in which the power feeding coil L1 is not excited. That is, the excitation coil E1 makes the resonator R1a and the resonator R1b adjacent in the row direction and the column direction among the plurality of resonators R1 to generate the alternating magnetic field with different resonance frequencies from each other in a frequency band in which the power feeding coil L1 inside is not excited.

Thus, when the driving frequency of the power feeding coil L1 is close to the frequency of the two sine wave signals output by the signal generator, the resonance coils M1 of the plurality of resonators R1 are excited by a very strong magnetic field for power transmission generated by the power feeding coil L1. In this way, a large current will flow to the plurality of resonators R1 and concerns rise that the resonators R1 may be destroyed. In addition, in the present embodiment, the frequencies of the two sine wave signals output by the signal generator SG is set to be a high frequency with a different order of magnitude from the driving frequency of the power feeding coil L1 (i.e., the frequency band in which the power feeding coil L1 is not excited), thus, the plurality of resonators R1 has a high impedance with respect to the strong magnetic field for power transmission generated by the power feeding coil L1 so that no current flows. Further, the plurality of resonators R1 are only syntonized with frequencies of the two sine wave signals output by the signal generator SG with which the excitation coil E1 is excited, so that the plurality of resonators R1 is excited and a current flows. Therefore, the damage due to the large current flowing to the plurality of resonators R1 can be prevented. In addition, in the present embodiment, the two frequencies output by the signal generator SG with which the excitation coil E1 is excited is set to be one with the order of magnitude being higher than that of the driving frequency of the power feeding coil L1. However, these two frequencies are not limited thereto and can be also set as one with the order of magnitude being lower than that of the driving frequency of the power feeding coil L1. At that time, the resonance frequency fr1 of the resonator R1a and the resonance frequency fr2 of the resonator R1b are also set as ones with the order of magnitude being lower than that of the driving frequency of the power feeding coil L1. Anyway, it is practical if the two frequencies output by the signal generator SG with which the excitation coil E1 is excited are set to within a frequency band in which the power feeding coil L1 is not excited.

The frequency response analyzer A100 is connected to two terminals in the resonance capacitor C1 of the plurality of resonators R1. If the frequency response analyzer A100 is used, the impedance value and the Q value can be measured in the plurality of resonators R1. In the present embodiment, the frequency response analyzer A100 is used to detect the foreign metals. Specifically, the impedance value and the Q value at the resonance frequency of the resonator R1 when no foreign metal is present are memorized. Then, the impedance values and Q values measured by the frequency response analyzer A100 are compared and the presence of the foreign metals can be determined based on the changes of these values. More specifically, if a foreign metal is present, the impedance value as measured by the frequency response analyzer A100 will increase and the Q value will decrease. If thresholds capable of determining whether a foreign metal are present or not is predetermined with respect to the impedance value and the Q value, then the presence of a foreign metal can be determined based on these thresholds. In this respect, if the frequency response analyzer A100 is used to measure the electric properties of the plurality of resonators R1 (i.e., the impedance value and the Q value), it is easy to detect the foreign metals.

As described above, in the power feeding coil unit L100 of the present embodiment, the excitation coil E1 makes the resonators R1a and R1b which are adjacent in the row direction and the column direction among the plurality of resonators R1 to generate an alternating magnetic field with resonance frequencies different from each other within a frequency band in which the power feeding coil L1 is not excited. Thus, as each resonator R1a/R1b can be prevented from influencing each other even if the plurality of resonators R1 are disposed without gaps in the area for metal detection, each resonator R1a/R1b can be prevented from generating multiple resonance frequencies and the decrease of the Q value can be inhibited as well. As a result, the accuracy in detecting foreign matter can be improved when the power is transmitted in a contactless manner.

The Second Embodiment

Figure 4:
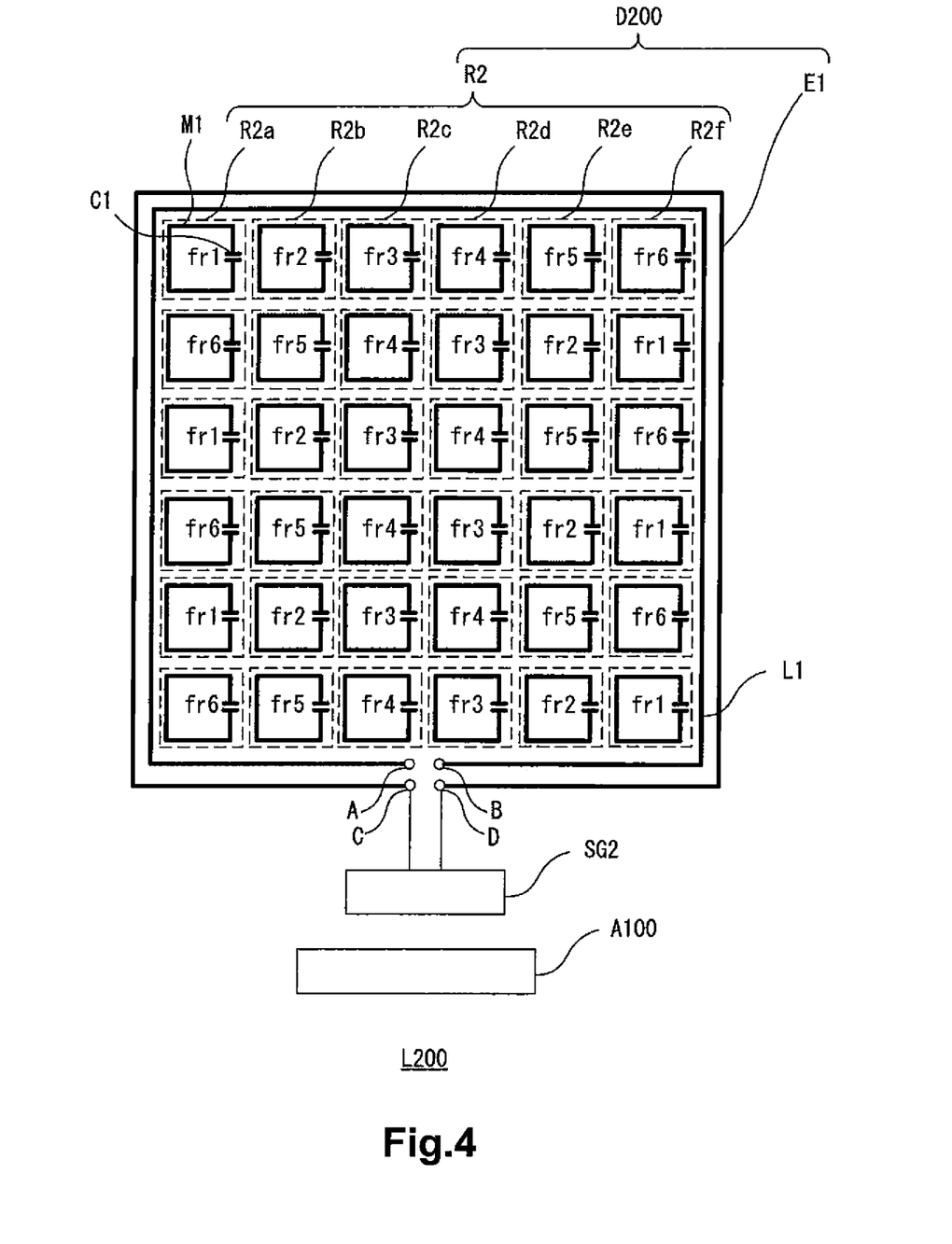
FIG. 4 is a schematic constitutional view showing the power feeding coil unit of the second embodiment viewed from the top in the present invention.

Hereinafter, the structure of the power feeding coil unit L200 in the second embodiment of the present invention will be described in detail with reference to FIG. 4. FIG. 4 is a schematic constitutional view showing the power feeding coil unit of the second embodiment viewed from the top in the present invention.

As the same as the power feeding coil unit L100 of the first embodiment, the power feeding coil unit L200 is provided with a power feeding coil L1, an apparatus D200 for detecting foreign matter, a signal generator SG2 and a frequency response analyzer A100. The structures of the power feeding coil L1 and the frequency response analyzer A100 are the same with those in the power feeding coil unit L100 of the first embodiment. In the present embodiment, what is different from the first embodiment is that a plurality of resonators R2 of the apparatus D200 for detecting foreign matter are provided with a plurality of resonators R2a to R2f and the signal generator SG2 outputs six sine wave signals with different frequencies. Hereinafter, the description will be focused on the points different from those of the first embodiments.

The apparatus D200 for detecting foreign matter is disposed on one side of the power feeding coil L1 at the side facing the power receiving coil L2. That is, the apparatus D200 for detecting foreign matter is disposed between the power feeding coil L1 (power feeding side) and the power receiving coil L2 (power receiving side). The apparatus D200 for detecting foreign matter is formed by, for example, a copper-clad multilayered substrate and is provided with a plurality of resonators R2 and an excitation coil E1.

The plurality of resonators R2 are disposed in rows and columns to cover at least the area interlinking with the magnetic flux generated by the power feeding coil L1. In other words, the plurality of resonators R2, as shown in FIG. 4, is disposed in rows and columns in the in-plane direction. In the present embodiment, the plurality of resonators R2 are composed of six resonators, i.e., the resonators R2a to R2f. Each of the resonators R2a to R2f have a single resonance frequency within a frequency band in which each power feeding coil L1 is not excited, and these single resonance frequencies are set as resonance frequencies fr1 to fr6 which are different from each other. As shown in FIG. 4, these resonators R2a to R2f are disposed in 6 rows×6 columns. Specifically, in the first, the third and fifth row, the resonators R2a, R2b, R2c, R2d, R2e and R2f are disposed in sequence from the left side as shown in the figure. Then, in the second, the forth and sixth row, the resonators R2f, R2e, R2d, R2c, R2b and R2a are disposed in sequence from the left side as shown in the figure. That is, the sequence of the resonators R2a to R2f in the first, the third and fifth row is reversed to that in the second, the forth and sixth row. In addition, the structures of the resonance coils M1 and the resonance capacitors C1 which constitute the resonators R2a to R2f are the same with those in the first embodiment. Further, as the same as the first embodiment, the plurality of resonators R2 can also be disposed in rows and columns to cover a wider area than that defined by the wound wire of the power feeding coil L1. In that case, not only the foreign matter on the power feeding coil L1 but also those surrounding the power feeding coil L1 can be detected. Anyway, if the area where the plurality of resonators R2 are disposed in rows and columns can cover at least the area interlinking with the magnetic flux generated by the power feeding coil L1, it can be set at will. Furthermore, it is preferable that the resonators R2a to R2f are disposed in the row direction with the given sequence in the whole area for metal detection. However, as long as the effect of the present invention can be provided, the resonators R2a can be positioned adjacent to each other in the row direction or the column direction in part of the area for metal detection. Also, the resonators R2b, R2c, R2d, R2e or R2f can be disposed in such a manner.

The signal generator SG2 is switched with a certain interval (such as every 100 ms) and provides six sine wave signals with different frequencies to the excitation coil E1. The frequencies of these six sine wave signals are respectively set to be the same with any one of the resonance frequency fr1 of the resonator R2a, the resonance frequency fr2 of the resonator R2b, the resonance frequency fr3 of the resonator R2c, the resonance frequency fr4 of the resonator R2d, the resonance frequency fr5 of the resonator R2e and the resonance frequency fr6 of the resonator R2f. In this way, the excitation coil E1 receives these six sine wave signals with different frequencies outputs by the signal generator SG2 and is then excited to generate a magnetic field. With this magnetic field, an electromotive force is generated in the resonance coil M1 of each of the resonators R2a to R2f and then the current flows. In the present embodiment, the resonators R2a to R2f are disposed as described above. Because of the excitation coil E1 which receives the six sine wave signals with different frequencies output from the signal generator SG2 and is then excited, one resonator and its surrounding resonators are enabled to generate alternating magnetic fields with resonance frequencies different from each other among the plurality of resonators R2. For instance, as shown in FIG. 4, around the resonator R2e in the second column and the forth column, the resonators R2a is positioned at top left, the resonators R2b is positioned right above, the resonators R2c is positioned at top right, the resonators R2d is positioned at the right side, the resonators R2c is positioned at the bottom right, the resonators R2b is positioned right below, the resonators R2a is positioned at bottom left and the resonators R2f is positioned at the left side. Thus, the resonator R2e generates an alternating magnetic field via a resonance frequency different from those of the surrounding resonators R2a to R2d, R2f.

In the power feeding coil unit L200 of the present embodiment, the excitation E1 in the plurality of resonators R2 enables one resonator and the resonators surrounding it to generate alternating magnetic fields with resonance frequencies different from each other. Therefore, even if the plurality of resonators R2 are disposed in the area for metal detection without gaps, each of the resonators R2a to R2f will be further prevented from influencing each other. In this respect, the resonators R2a to R2f can be effectively prevented from generating several resonance frequencies and the decrease of the Q value can be further inhibited. Thus, the accuracy in detecting foreign matter can be further improved when the power is transmitted in a contactless manner.

The Third Embodiment

Figure 5:
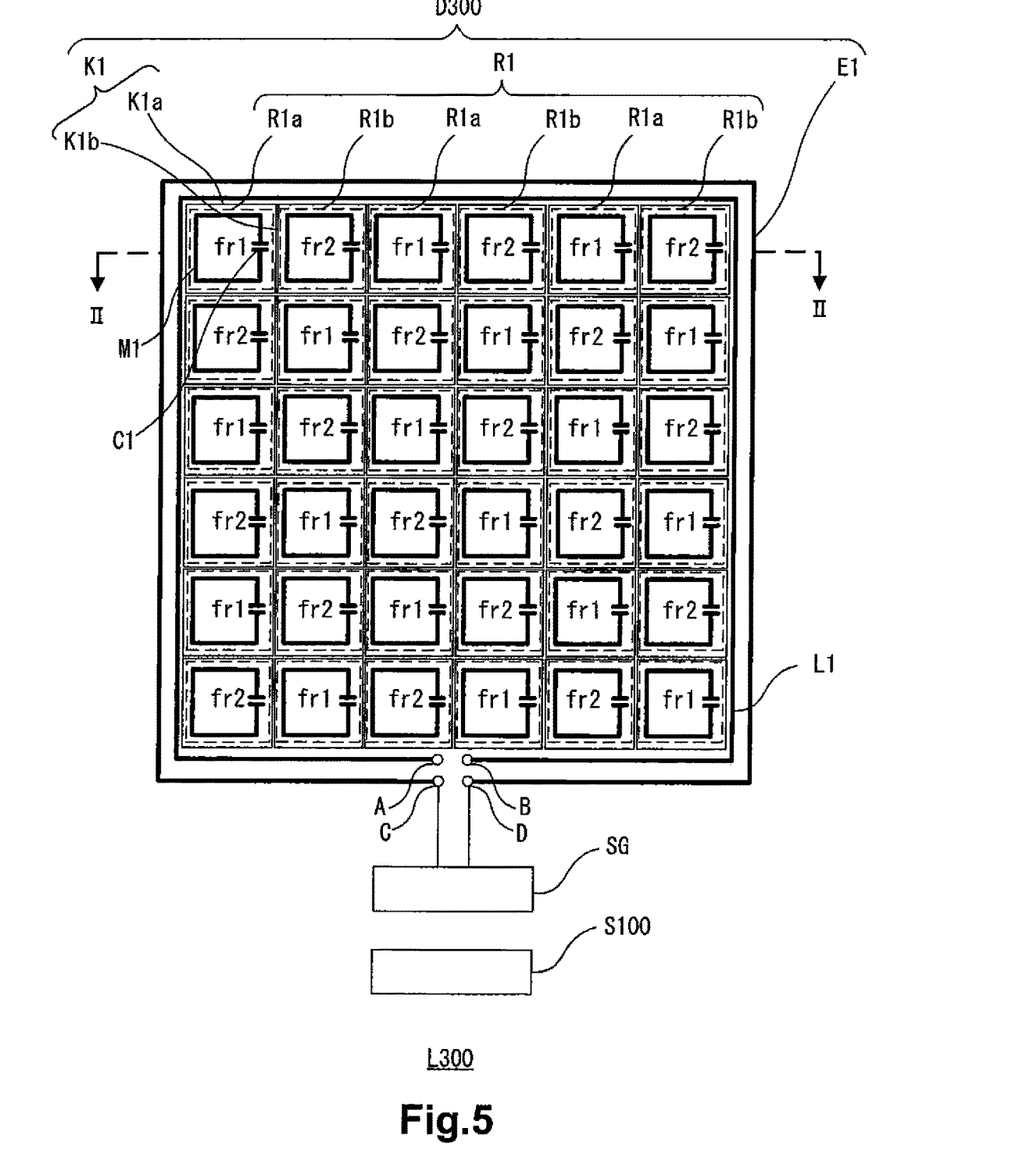
FIG. 5 is a schematic constitutional view showing the power feeding coil unit of the third embodiment viewed from the top in the present invention.
Figure 6:
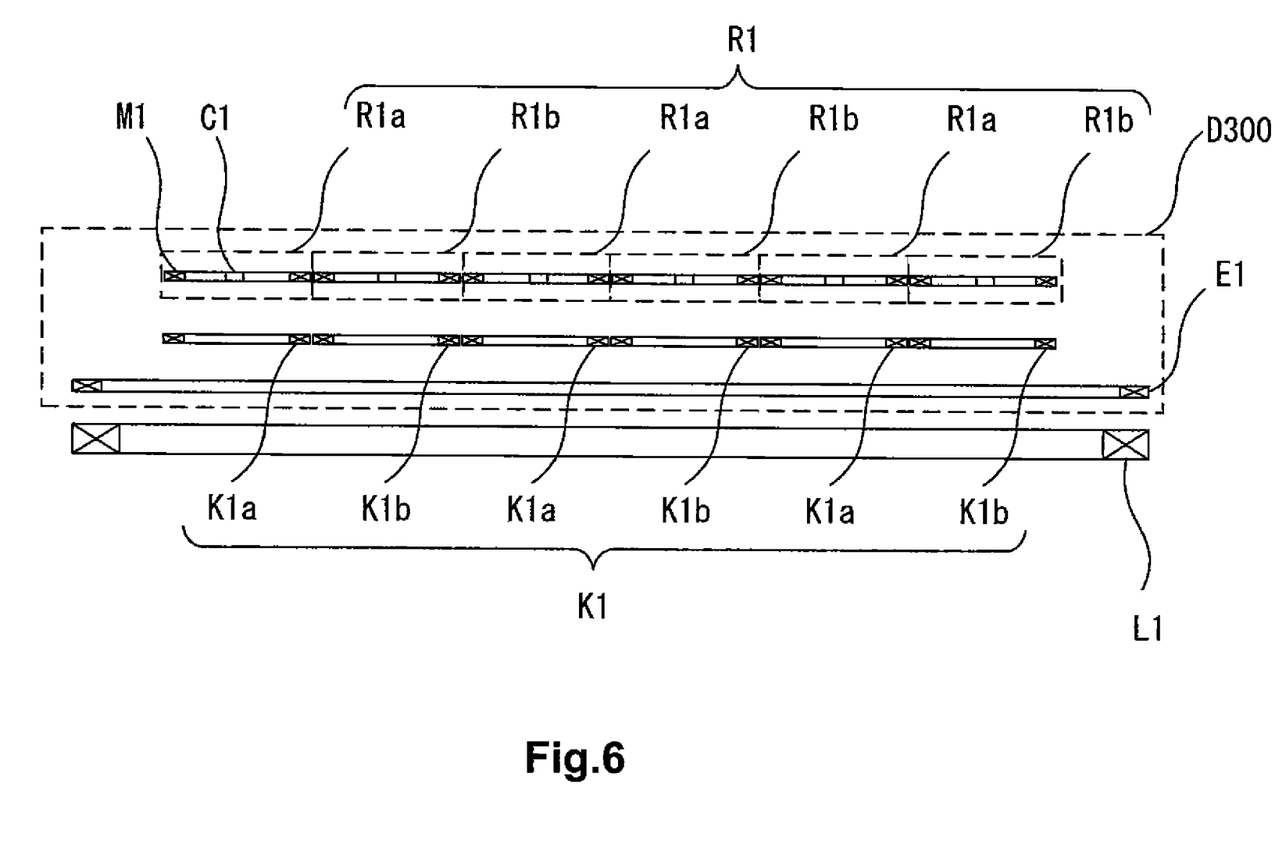
FIG. 6 is a schematic end face view showing the cutting section of the power feeding coil unit along the II-II line in FIG. 5.
Figure 7:
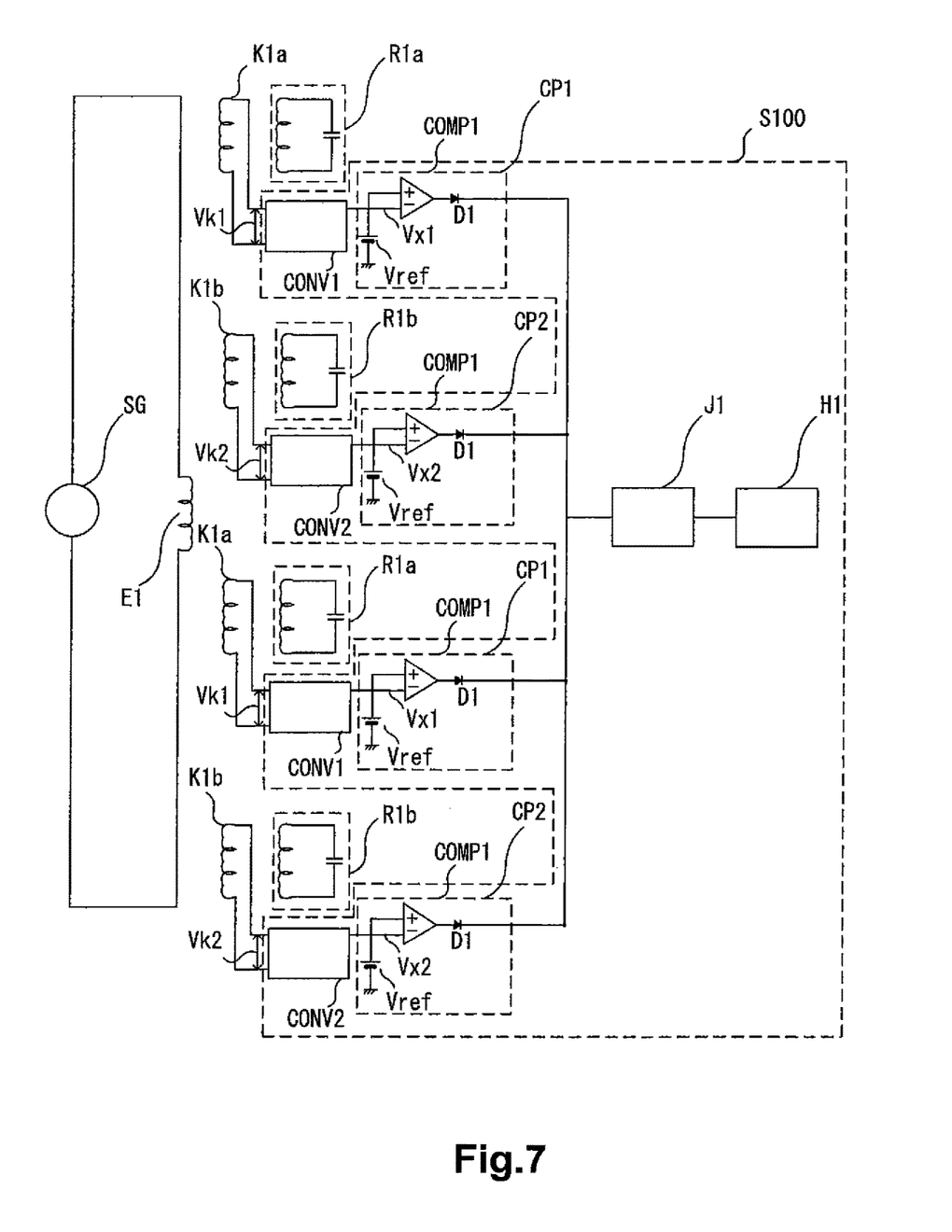
FIG. 7 is a schematic constitutional view showing the signal generator, the apparatus for detecting foreign matter and the system for detecting foreign matter in the power feeding coil unit of the third embodiment of the present invention.

Hereinafter, the structure of the power feeding coil unit L300 in the third embodiment of the present invention will be described in detail with reference to FIG. 5 to FIG. 7. FIG. 5 is a schematic constitutional view showing the power feeding coil unit of the third embodiment viewed from the top in the present invention. FIG. 6 is a schematic end face view showing the cutting section of the power feeding coil unit along the II-II line in FIG. 5. FIG. 7 is a schematic constitutional view showing the signal generator, the apparatus for detecting foreign matter and the system for detecting foreign matter in the power feeding coil unit of the third embodiment of the present invention.

As the same as the power feeding coil unit L100 of the first embodiment, the power feeding coil unit L300 is provided with a power feeding coil L1, an apparatus D300 for detecting foreign matter, a signal generator SG3 and a system S100 for detecting foreign matter. The structures of the power feeding coil L1 and the signal generator SG are the same with those in the power feeding coil unit L100 of the first embodiment. In the present embodiment, what is different from the first embodiment is that the apparatus D300 for detecting foreign matter is provided with a plurality of detecting coils K1 and the system S100 for detecting foreign matter is arranged instead of the frequency response analyzer A100. Hereinafter, the description will be focused on the points different from those of the first embodiments.

As shown in FIG. 6, the apparatus D300 for detecting foreign matter is disposed on the power feeding coil L1 at the side facing the power receiving coil L2. That is, the apparatus D300 for detecting foreign matter is placed between the power feeding coil L1 and the power receiving coil L2. The apparatus D300 for detecting foreign matter is formed by, for example, a copper-clad multilayered substrate and is provided with a plurality of resonators R1, an excitation coil E1 and a plurality of detecting coils K1. The structures of the plurality of resonators R1 and the excitation coil E1 are the same with those in the power feeding coil unit L100 of the first embodiment.

As shown in FIG. 5, each of the plurality of detecting coils K1 presents to be substantially square and is formed by, for example, pattern printing 4 turns of coils on a layer of the copper-clad multilayered substrate between the layer where the excitation coil M1 of the plurality of resonators R1 is formed and the layer where the excitation coil E1 is formed in a direction in which the power feeding coil L1 faces the power receiving coil L2. Each pattern of the plurality of detecting coils K1 is disposed in rows and columns to be electromagnetically (magnetically) coupled to each of the plurality of resonators R1. That is, each pattern of the plurality of detecting coils K1 faces each resonance coil M1 of the plurality of resonators R1. In addition, if the axis of each pattern in the plurality of detecting coils K1 is consistent with that of each resonance coil M1 in the plurality of resonators R1, then the electromagnetic coupling will be strong which is preferable. The plurality of detecting coils K1 are electromagnetically coupled to each of the plurality of resonators R1, so the alternating current flows to the resonator excited by the excitation coil E1 so that the electromotive force is generated and the alternating current flows. As such, the alternating signal Vk is output to a plurality of AC/DC converter CONV to be described later from the plurality of detecting coils K1. At that time, the detecting coil K1a disposed opposing to the resonator R1a outputs an alternating signal Vk1 and the detecting coil K1b disposed opposing to the resonator R1b outputs an alternating signal Vk2.

As shown in FIG. 7, the system S100 for detecting foreign matter is provided with a plurality of AC/DC converter CONV, a plurality of comparator circuits CP, a decider J1 and a display H1. In the present embodiment, the system for detecting foreign matter with two resonators R1a and two resonators R1b are shown in the figures. However, the system S100 for detecting foreign matter can also be provided with respect to the amount of a plurality of resonators R1a and R1b.

The plurality of AC/DC converters CONV are connected to both ends of each coil in the plurality of detecting coils K1. The plurality of AC/DC converters CONV converts the alternating current signal Vk output from the plurality of detecting coils K1 to a direct current signal Vx and then outputs the direct current signal Vx to the plurality of comparator circuits CP which are to be described later. Specifically, the plurality of AC/DC converters CONV have a plurality of AC/DC converters CONV1 connected to the detecting coil K1a and a plurality of AC/DC converters CONV2 connected to the detecting coil K1b. Further, the alternating current signal Vk1 is converted to a direct current signal Vx1 by the plurality of AC/DC converters CONV1, and the alternating current signal Vk2 is converted to a direct current signal Vx2 by the plurality of AC/DC converters CONV2.

As shown in FIG. 7, the plurality of comparator circuits CP are respectively composed of a comparator COMP1 and a diode D1. The direct current signal Vx output from the plurality of AC/DC converters CONV is input to the inverted input terminal of the comparator COMP1, and the reference voltage Vref is input into the non-inverted input terminal of the comparator COMP1. The positive terminal of the diode D1 is connected to the output terminal of the comparator COMP1. In addition, the negative terminal of the diode D1 is connected to the decider J1 described later. The plurality of comparator circuits CP with such a structure compares the direct current signal Vx input to the inverted input terminal of the comparator COMP1 and the reference voltage Vref input to the non-inverted input terminal. When the direct current signal Vx is higher than the reference voltage Vref, a signal of a low level is output from the output terminal of the comparator COMP1 to the decider J1 to be described later via the diode D1. In contrast, when the direct current signal Vx is lower than the reference voltage Vref, a signal of a high level is output from the output terminal of the comparator COMP1 to the decider J1 to be described later via the diode D1. Specifically, the plurality of comparator circuits CP are provided with a plurality of comparator circuits CP1 where the direct current signal Vx1 output from the plurality of AC/DC converters CONV1 is input to the inverted input terminal of the comparator COMP1 and a plurality of comparator circuits CP2 where the direct current signal Vx2 output from the plurality of AC/DC converters CONV2 is input to the inverted input terminal of the comparator COMP1.

The decider J1 is connected to the plurality of comparator circuits CP. In this way, since the decider J1 is jointly connected to the plurality of comparator circuits CP, when all the signals output from the plurality of comparator circuits CP have a low level, a signal of a low level is input to the decider J1. In addition, when any of the signals output from the plurality of comparator circuits CP have a high level, a signal of a high level is input to the decider J1. Specifically, when the signal generator SG outputs a sine wave signal of 3000 [kHz], if all the signals as the result of the comparison between the direct current signal Vx1 of the plurality of comparator circuits CP1 and the reference voltage Vref have a low level, it is decided that no foreign metal is present. Otherwise, when any one of the signals as the result of the comparison between the direct current signal Vx1 of the plurality of comparator circuits CP1 and the reference voltage Vref has a high level, it is decided that a foreign metal is present. Further, when the signal generator SG outputs a sine wave signal of 6000 [kHz], if all the signals as the result of the comparison between the direct current signal Vx2 of the plurality of comparator circuits CP2 and the reference voltage Vref have a low level, it is decided that no foreign metal is present. Otherwise, when any one of the signals as the result of the comparison between the direct current signal Vx2 of the plurality of comparator circuits CP2 and the reference voltage Vref has a high level, it is decided that a foreign metal is present. In this way, the decider J1 analyzes the wave form of the signal output from the plurality of comparator circuits CP to determine whether a foreign metal is present. Then, the result (whether a foreign metal is present or not) from the decider J1 is output to the display H1.

The display H1 is connected to the decider J1. The display H1 is capable of telling the users the result (whether a foreign metal is present or not) given by the decider J1. For example, the display H1 is provided with indicator lights with colors like red and green (not shown) and can be performed as described below. That is, if the decider J1 determines that no foreign metal has been detected, then the green indicator light is lighted. If the decider J1 determines that a foreign metal has been detected, then the red indicator light is lighted. The user is informed of the presence of a foreign metal by the display H1 so that the user is enabled to intervene in the power supply of the apparatus S1 for contactless power transmission (keep it on or stop it). Further, other means in which the presence of the foreign metal is not determined by the decider J1 and the display H1 can be performed as described below. That is, when the plurality of comparator circuits CP output a signal of a low level, the action of the power conversion circuit INV will be kept on. When the plurality of comparator circuits CP output a signal of a high level, the action of the power conversion circuit INV is stopped.

Figure 8:
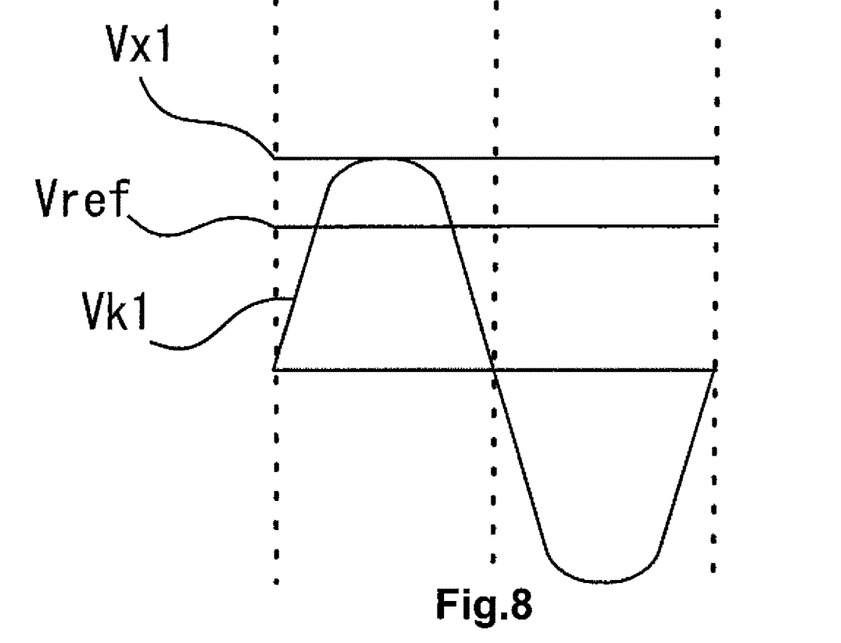
FIG. 8 is a waveform diagram illustrating the waveform of the signals output from a plurality of detecting coils and a plurality of AC/DC converter when the signal generator outputs sine wave signals of 3000 [kHz].
Figure 9:
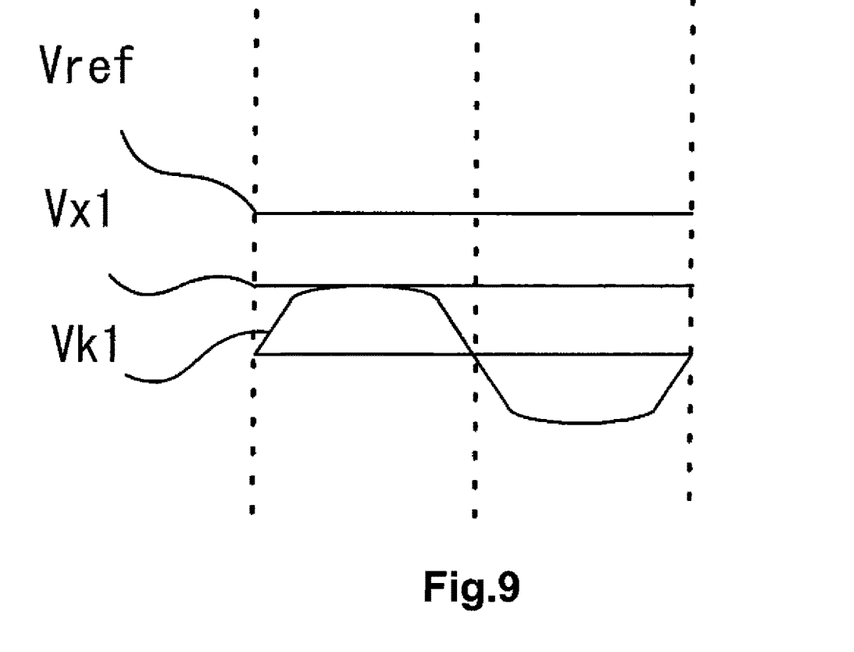
FIG. 9 is a waveform diagram illustrating the waveform of the signals output from a plurality of detecting coils and a plurality of AC/DC converter when the signal generator outputs sine wave signals of 3000 [kHz].
Figure 10:
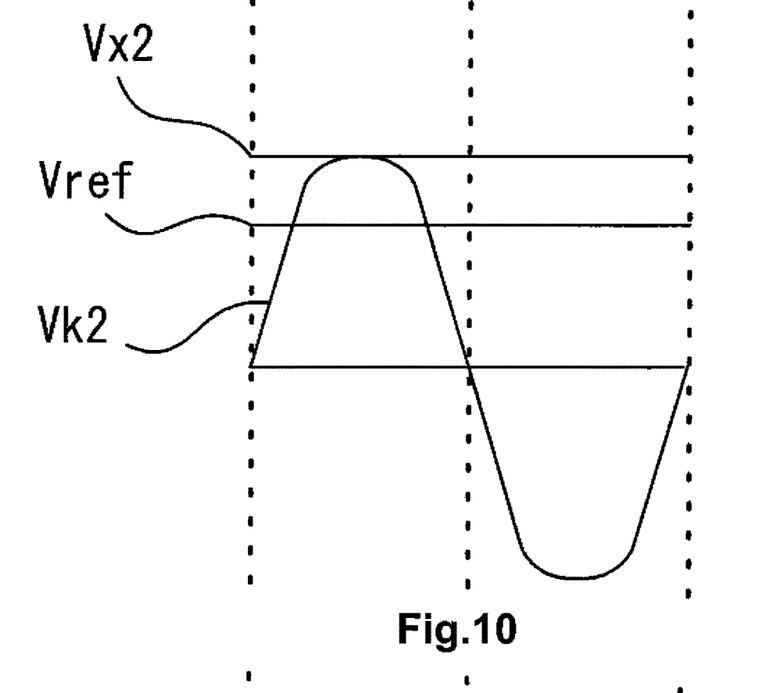
FIG. 10 is a waveform diagram illustrating the waveform of the signals output from a plurality of detecting coils and a plurality of AC/DC converter when the signal generator outputs sine wave signals of 6000 [kHz].
Figure 11:
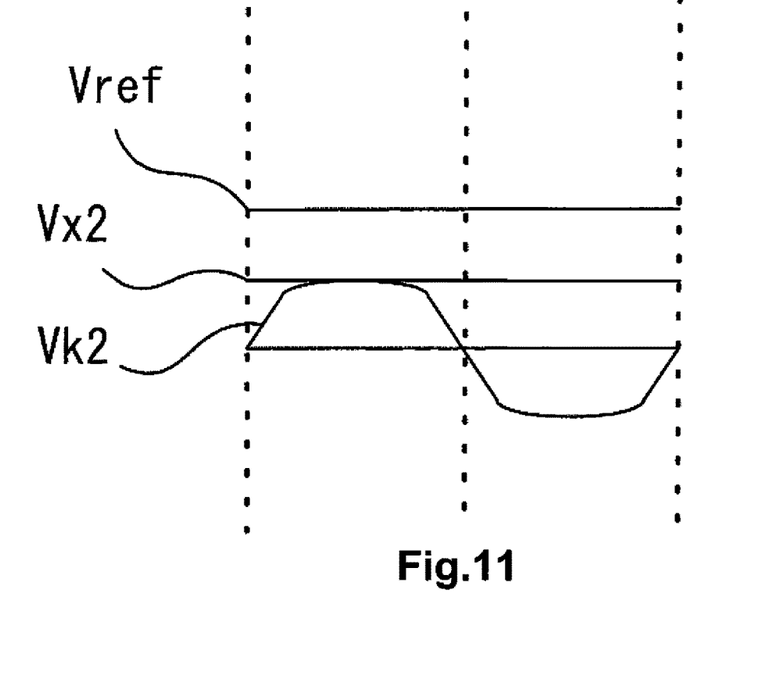
FIG. 11 is a waveform diagram illustrating the waveform of the signals output from a plurality of detecting coils and a plurality of AC/DC converter when the signal generator outputs sine wave signals of 6000 [kHz].

Here, the waveform of the signal from the system S100 for detecting foreign matter in the power feeding coil unit L300 of the present embodiment will be described below with reference to FIG. 8 to FIG. 11. FIG. 8 and FIG. 9 are waveform diagrams illustrating the waveform of the signals output from the plurality of detecting coils and the plurality of AC/DC converter when the signal generator outputs sine wave signals of 3000 [kHz]. FIG. 10 and FIG. 11 are waveform diagrams illustrating the waveform of the signals output from the plurality of detecting coils and the plurality of AC/DC converter when the signal generator outputs sine wave signals of 6000 [kHz].

Each signal waveform which appears when the signal generator SG outputs sine wave signals of 3000 [kHz] (100 ms) will be described as follows. If the sine wave signal of 3000 [kHz] is provided to the excitation coil E1 from the signal generator SG, the resonator R1a comes into resonance state and the resonance current flows. Also, an electromotive force is generated in the detecting coil K1a disposed opposing to the resonator R1a and an alternating current flows. The alternating signal Vk1 is output to the AC/DC converter CONV1 from the detecting coil K1a and then converted to the direct current signal Vx1 by the AC/DC converter CONV1. In this way, the plurality of comparator circuits CP1 compare the direct current signal Vx1 input to the inverted input terminal of the comparator COMP1 and the reference voltage Vref input to the non-inverted input terminal. As shown in FIG. 8, when no foreign metal is present, the direct current signal Vx1 becomes higher than the reference voltage Vref so that all the signals of low levels are output from the plurality of comparator circuits CP1. Further, when a foreign metal is present, the resonance frequency of the resonator R1a becomes higher than 3000 [kHz] or the Q value decreases at the same time. Also, as shown in FIG. 9, as the direct current signal Vx1 becomes lower than the reference voltage Vref, the signals of high levels are output from the plurality of comparator circuits CP1.

Then, each signal waveform which appears when the signal generator SG outputs sine wave signals of 6000 [kHz] (100 ms) will be described as follows. If the sine wave signal of 6000 [kHz] is provided to the excitation coil E1 from the signal generator SG, the alternating current flows to the resonator R1b via the magnetic field generated by the excitation coil E1. Also, an electromotive force is generated in the detecting coil K1b disposed opposing to the resonator R1b and an alternating current flows. The alternating signal Vk2 is output to the AC/DC converter CONV2 from the detecting coil K1b and then converted to the direct current signal Vx2 by the AC/DC converter CONV2. In this way, the plurality of comparator circuits CP2 compare the direct current signal Vx2 input to the inverted input terminal of the comparator COMP1 and the reference voltage Vref input to the non-inverted input terminal. As shown in FIG. 10, when no foreign metal is present, the direct current signal Vx2 becomes higher than the reference voltage Vref so that all the signals of low levels are output from the plurality of comparator circuits CP2. Further, when a foreign metal is present, the resonance frequency of the resonator R1b becomes higher than 6000 [kHz] and the Q value decreases at the same time. Also, as shown in FIG. 11, as the direct current signal Vx2 becomes lower than the reference voltage Vref, the signals of high levels are output from the plurality of comparator circuits CP2.

As described above, in the power feeding coil L300 of the present embodiment, the apparatus D300 for detecting foreign matter is further provided with a plurality of detecting coils K1 and the plurality of detecting coils K1 are respectively electromagnetically coupled to each of the plurality of resonators R1. In this respect, as the means for measuring the Q value is not directly connected to the plurality of resonators R1 and it is possible to measure the Q values of the plurality of resonators R1, the decrease of the Q values of the plurality of resonators R1 can be further inhibited without changing the resonance frequencies of the plurality of resonators R1.

Furthermore, the present invention does not have to be not limited to the described embodiments, and various modifications within the spirit of the invention are practical. For example, the present embodiment is described by using an example in which an apparatus for detecting foreign matter is applied to a coil unit for contactless power transmission from power feeding side to power receiving side. However, the present invention is not limited thereto. The apparatus for detecting foreign matter of the present invention can also be applicable to detect the foreign metals present in the food, medicines and industrial materials which are wrapped in packing materials.

The coil unit of the present invention can be used in an apparatus for detecting foreign matter, equipped on contactless power feeding device for electric vehicle, which is used for power transmission and charging of the secondary battery in a contactless manner from the ground to a parking electric vehicle. The coil unit of the present invention can also be used in an apparatus for detecting foreign matter used to detect the foreign metals present in the food, medicines and industrial materials which are wrapped in packing materials.

DESCRIPTION OF REFERENCE NUMERALS 100 power feeding apparatus
200 power receiving apparatus
A to D terminal
A100 frequency response analyzer
C1 resonance capacitor
COMP1 comparator
CONV, CONV1, CONV2 plurality of AC/DC converters
CP, CP1, CP2 plurality of comparator circuits
D1 diode
D100, D200, D300 the apparatus for detecting foreign matter
E1 excitation coil
H1 display
INV power conversion circuit
J1 decider
K1, K1a, K1b plurality of detecting coils
L1 power feeding coil
L100, L200, L300 power feeding coil unit
L2 power receiving coil
M1 resonance coil
R1, R1a, R1b, R2, R2a to R2f plurality of resonators
REC rectification circuit
S1 the apparatus for contactless power transmission
S100 the system for detecting foreign matter
SG, SG2 signal generator
VG voltage source

What is claimed is:

1. A coil unit, which is used for a contactless power transmission from a power feeding side to a power receiving side,
    comprising a coil for power transmission and an apparatus for detecting foreign matter,
    wherein, the apparatus for detecting foreign matter comprises a plurality of resonators comprising a resonance coil and a resonance capacitor, and an excitation coil for exciting the plurality of resonators,
    wherein, the plurality of resonators are disposed in rows and columns so as to cover at least an area interlinking with a magnetic flux generated by the coil for power transmission,
    the excitation coil makes resonators adjacent to each other in a row direction and a column direction among the plurality of resonators to generate an alternating magnetic field with resonance frequencies different from each other, the resonance frequencies being within a same frequency band, the coil for power transmission not being excited within the same frequency band, and
    wherein,
    the apparatus for detecting foreign matter further comprises a plurality of detecting coils,
    each of the plurality of detecting coils is disposed so as to be magnetically coupled to each resonator of the plurality of resonators.

2. The coil unit of claim 1, wherein,
    the excitation coil makes one resonator and the resonators which is disposed surrounding it among the plurality of resonators, to generate an alternating magnetic field with resonance frequencies different from each other.

* * * * *